(12) United States Patent
Sexton et al.

(10) Patent No.: US 6,567,686 B2
(45) Date of Patent: May 20, 2003

(54) METHOD FOR IMPROVING LUNG DELIVERY OF PHARMACEUTICAL AEROSOLS

(75) Inventors: Frederick Sexton, Fair Haven, NJ (US); Akwete L. Adjei, Bridgewater, NJ (US); Perry Arthur Genova, Chapel Hill, NC (US); Richard Joel Melker, Gainesville, FL (US); Johannes Hugo van Oostrom, Gainesville, FL (US); Ilona Maria Schmalfuss, Gainesville, FL (US); Anthony A. Mancuso, Gainesville, FL (US)

(73) Assignee: IEP Pharmaceutical Devices, Inc., Raleigh, NC (US)

( * ) Notice: Subject to any disclaimer, the term of this patent is extended or adjusted under 35 U.S.C. 154(b) by 0 days.

(21) Appl. No.: 09/825,011

(22) Filed: Apr. 3, 2001

(65) Prior Publication Data

US 2001/0035183 A1 Nov. 1, 2001

Related U.S. Application Data

(60) Provisional application No. 60/194,235, filed on Apr. 3, 2000.

(51) Int. Cl.[7] .................................................. A61B 5/05
(52) U.S. Cl. ...................................... 600/420; 128/922
(58) Field of Search .............................. 600/420, 419, 600/410, 398, 407; 128/922

(56) References Cited

U.S. PATENT DOCUMENTS

| 4,642,778 A | 2/1987 | Hieftje et al. |
|---|---|---|
| 4,734,646 A | 3/1988 | Shenoy et al. |
| 4,926,852 A | 5/1990 | Zoltan et al. |
| 5,040,527 A | 8/1991 | Larson et al. |
| 5,203,323 A | 4/1993 | Tritle |
| 5,311,131 A | 5/1994 | Smith |
| 5,320,094 A | 6/1994 | Laube et al. |
| 5,364,838 A | 11/1994 | Rubsamen |
| 5,419,315 A | 5/1995 | Rubsamen |
| 5,427,089 A | 6/1995 | Kraemer |
| 5,494,030 A * | 2/1996 | Swartz et al. ............... 324/316 |
| 5,672,581 A | 9/1997 | Rubsamen et al. |
| 5,694,934 A | 12/1997 | Edelman |
| 5,789,921 A * | 8/1998 | Albert et al. ............... 324/300 |
| 5,988,168 A | 11/1999 | Bair |

FOREIGN PATENT DOCUMENTS

WO     WO 99/53332     10/1999

OTHER PUBLICATIONS

Fleming J.S. et al., "Three–Dimensional Description of Pulmonary Deposition of Inhaled Aerosol Using Data From Multimodality Imaging", *Journal of Nuclear Medicine*, vol. 37, No. 5, May 1996 pp. 873–877.

(List continued on next page.)

Primary Examiner—Henry C. Yuen
Assistant Examiner—Mahmoud Gimie
(74) Attorney, Agent, or Firm—Frommer Lawrence & Haug, LLP; Ronald R. Santucci

(57) ABSTRACT

Disclosure is made of a method employing real-time imaging techniques such as Magnetic Resonance Imaging in order to investigate the effect of air way structures or administration and respiratory drugs when administered by oral inhalation. The information obtained from the practice of this method yields the criteria that can be used, among other things, to design more efficient aerosol drug delivery systems which optimize the amount of medicine delivered to the lung.

14 Claims, 11 Drawing Sheets

OTHER PUBLICATIONS

Fleming J. S. et al., "Evaluation of the Accuracy and Precision of Lung Aerosol Deposition Measurements From Planar Radionuclide Imaging Using Simulation Physics in Medicine and Biology" *IOP Publishing*, vol. 43, No. 8, Aug. 1998, pp. 2423–2429.

Misselwitz B. et al., "Magnetic Resonance Imaging of Pulmonary Ventilation", *Investigative Radiology*, vol. 32, No. 12, Dec. 1997, pp. 797–801.

International Search Report prepared by European Patent Office for corresponding international application, PCT/US01/40433, mailed Apr. 18, 2002.

* cited by examiner

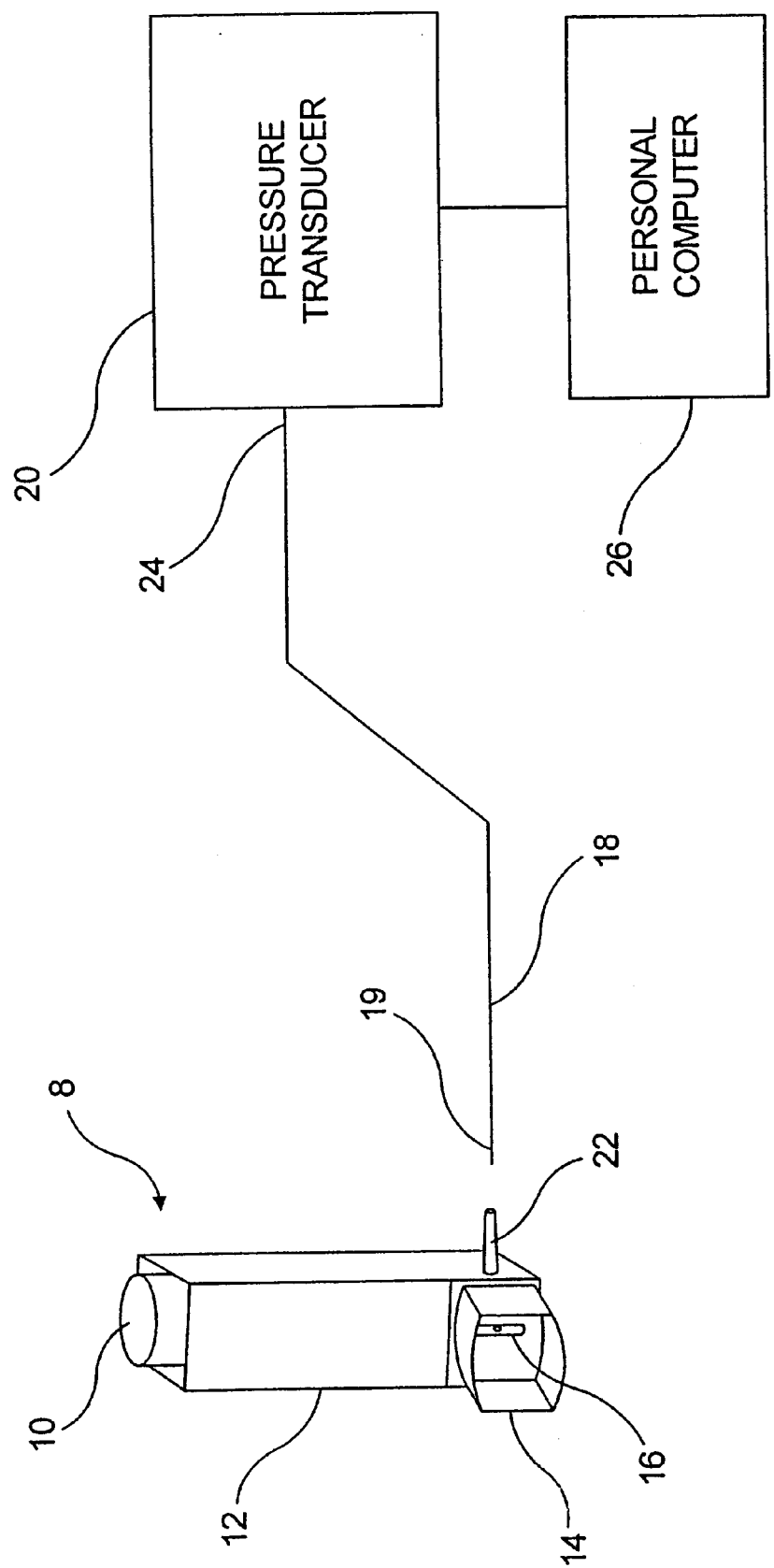

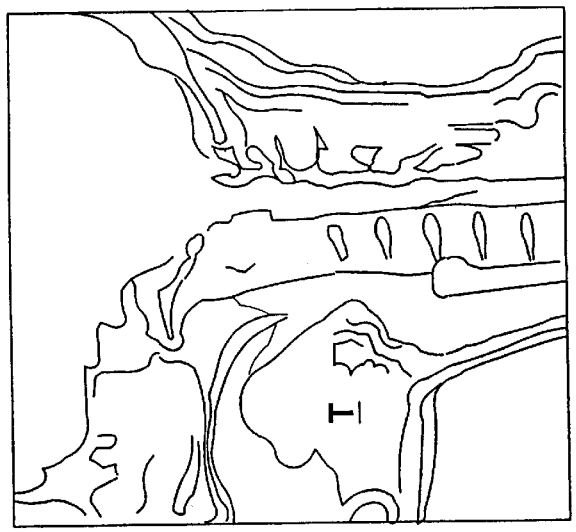
FIG. 8 Further Inspiration
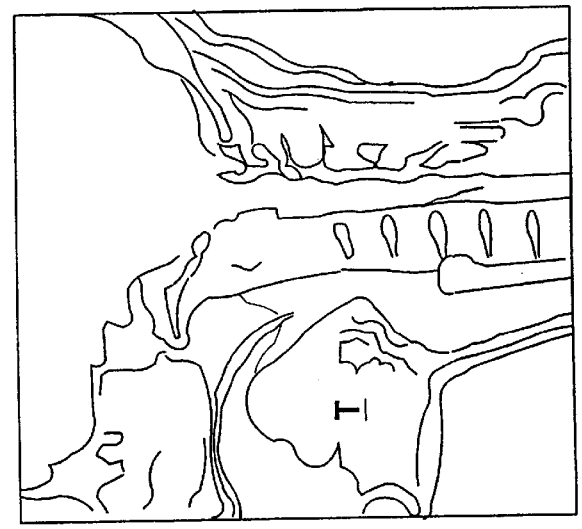
FIG. 7 Further Inspiration
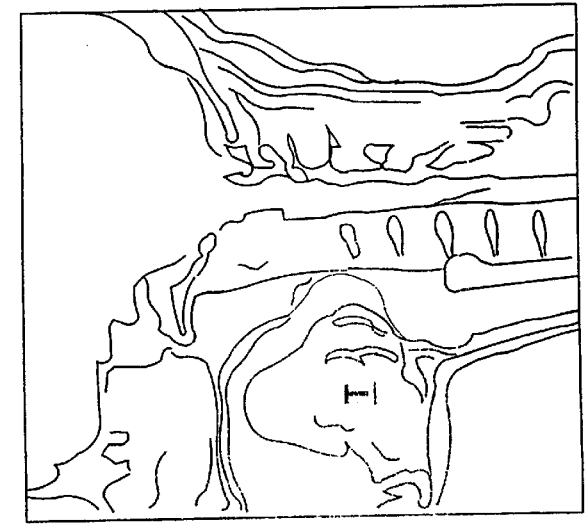
FIG. 6 Puffing in

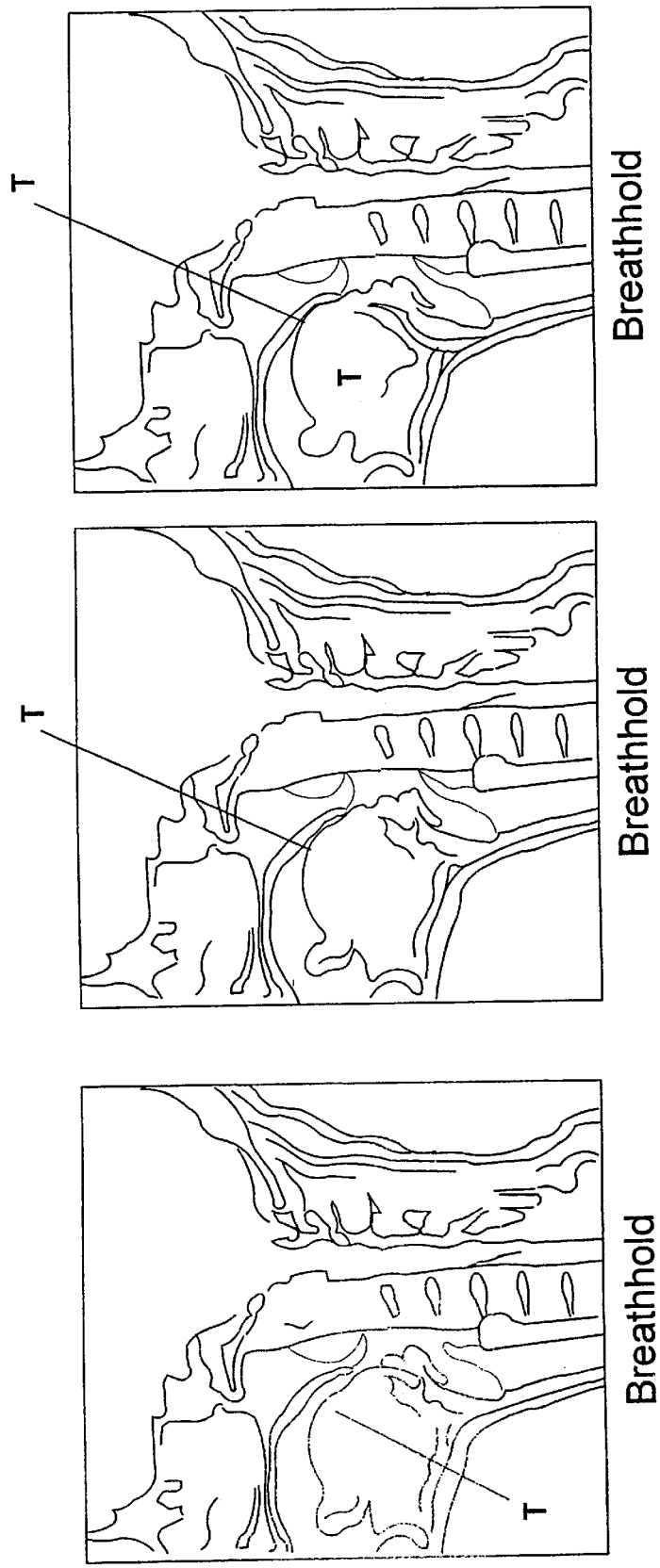

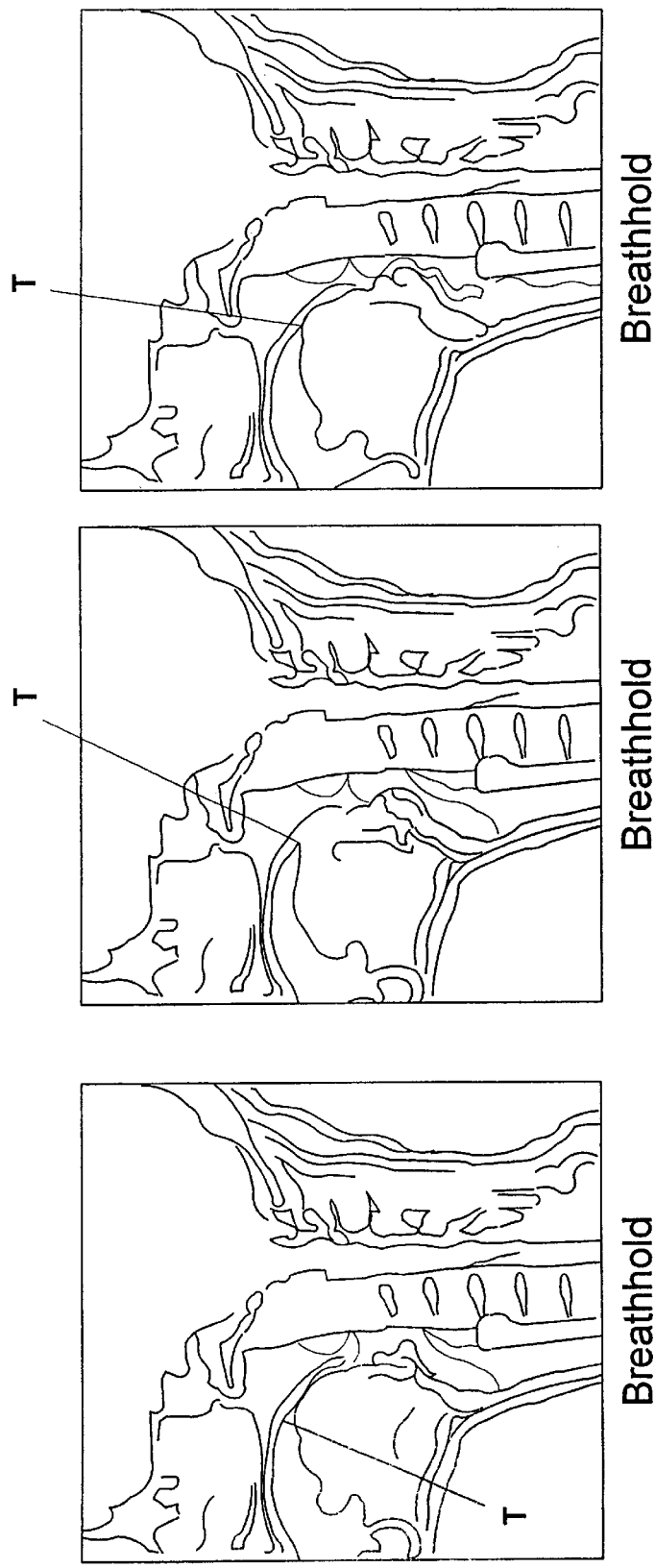

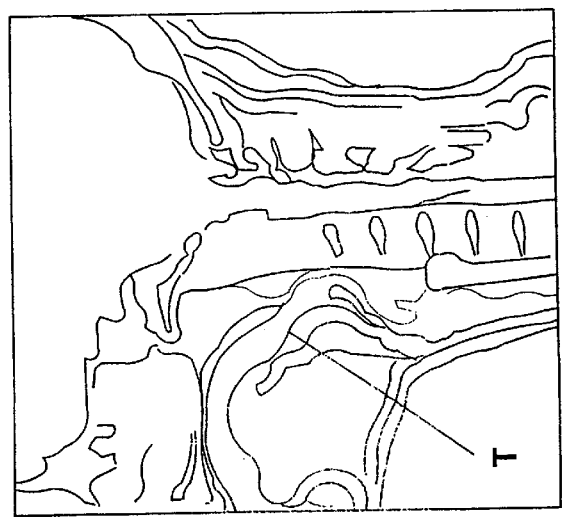
FIG. 18 Slow expiration
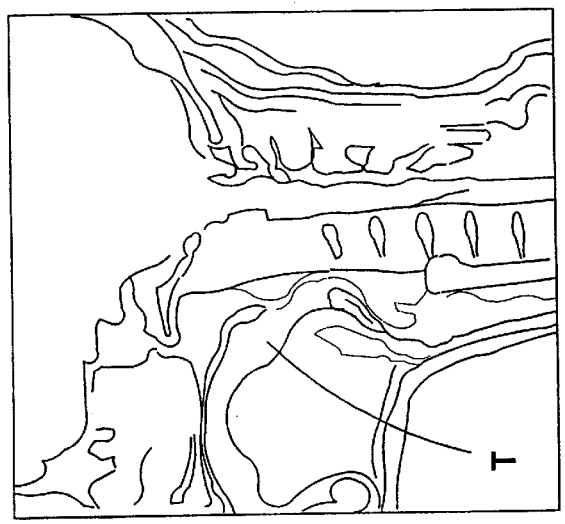
FIG. 19 Slow expiration
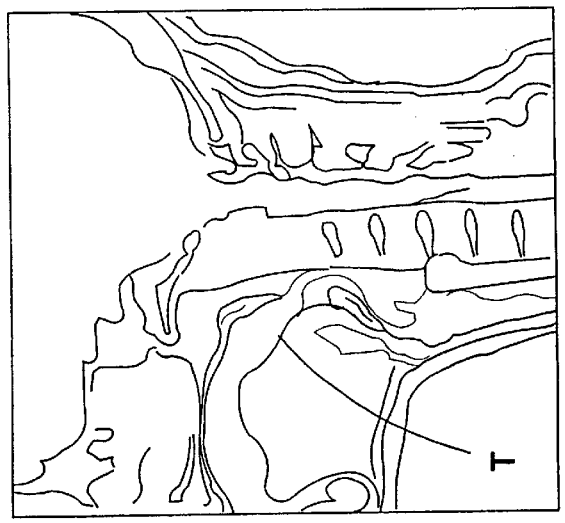
FIG. 20 Slow expiration Slow expiration

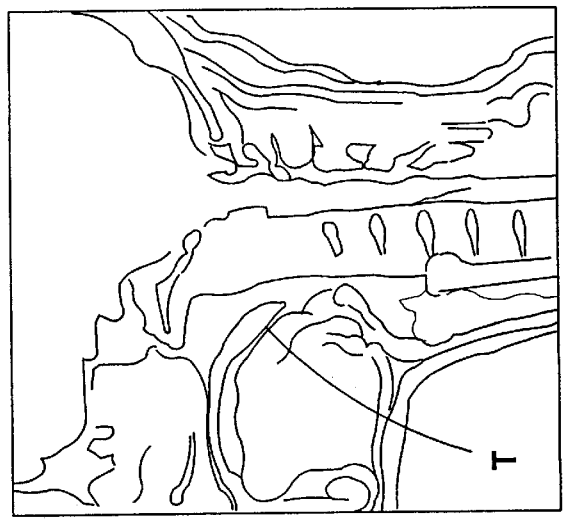
FIG. 26 End of expiration
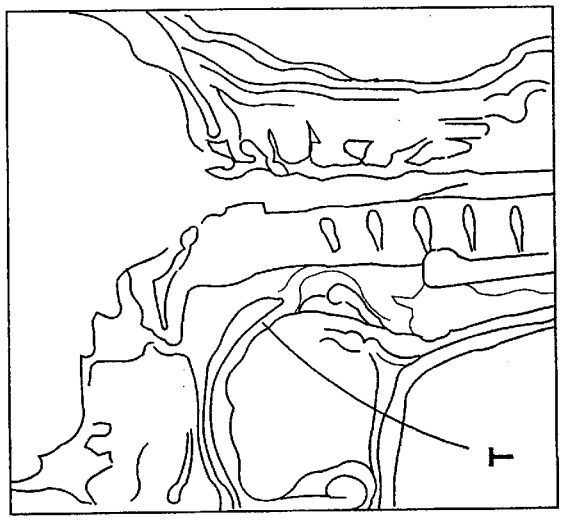
FIG. 25 End of expiration
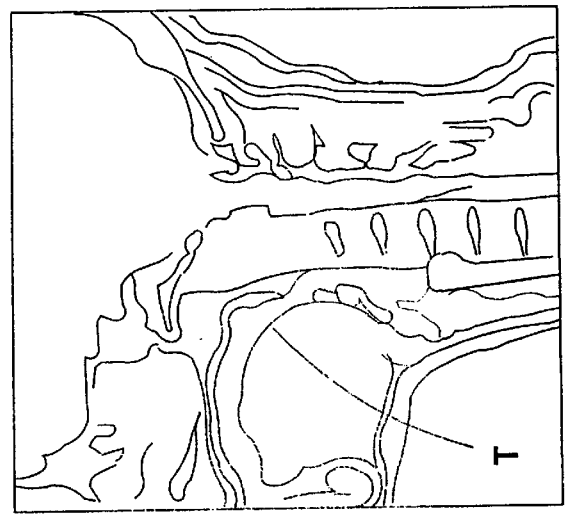
FIG. 24 End of expiration

METHOD FOR IMPROVING LUNG DELIVERY OF PHARMACEUTICAL AEROSOLS

BACKGROUND OF THE INVENTION

This application claims priority from U.S. Provisional Application Ser. No. 60/194,235, entitled METHOD FOR IMPROVING LUNG DELIVERY OF PHARMACEUTICAL AEROSOLS, filed Apr. 3, 2000, the disclosure of which is incorporated herein by reference.

FIELD OF THE INVENTION

The present invention relates to a method of monitoring the role of upper oropharyngeal and laryngeal geometry for the retention and elimination of respiratory drugs when administered by oral inhalation. The method is based primarily upon acquiring real-time MRI images of human subjects while using aerosol inhalation devices. From these image sets and the data accumulated, one may determine design criteria of the delivery device to optimize the delivery of pharmaceutical aerosol to targeted pulmonary sites. Condition variables include particle size, device attributes such as mouthpiece shape and resistance to flow, aerosol exit velocity, and inhalation flow rate.

DESCRIPTION OF THE PRIOR ART

Magnetic resonance imaging techniques have become widely accepted in medical practice as a means of investigating structural and anatomical differences in body tissues and organs: Justin P. Smith, "Magnetic Resonance Imaging Using Pattern Recognition" U.S. Pat. No. 5,311,131; Hiftje, et al. "Method And Device For Spectral Reconstruction" U.S. Pat. No. 4,642,778; and Shendy et al. "Method For Obtaining T1-Weighted and T2-Weighted MNR Images For A Plurality Of Selected Planes In The Course Of A Single Scan" U.S. Pat. No. 4,734,646. In a typical medical application, a patient is placed within the bore of a large, circular magnet. The magnet creates a static magnetic field that extends along the long (head-to-toe) axis of the patient's body. An antenna (e.g., a coil of wire) is also positioned within the bore of the large magnet, and is used to create an oscillating radio frequency field that selectively excites hydrogen atoms (protons) in the patient's body into oscillation. The oscillating field is then turned off, and the antenna is used as a receiving element, to detect the proton oscillations as a function of position within the body. Typically, the intensity of the oscillations is measured throughout a two-dimensional plane. When the intensities are displayed as a function of position in this plane, the result is an image that often bears a striking resemblance to the actual anatomic features in that plane. The intensity of proton oscillations detected at a given point in the patient's body is proportional to the proton density at that point. Because different types of tissues have different proton densities, different tissue types usually have different image intensities, and therefore appear as distinct structures in the MR image. However, the signal intensity also depends on physical and chemical properties of the tissues being imaged. In a simplified model of MRI, the detected signal intensity, as a function of position coordinates x and y in the plane being imaged, is proportional to $$(1-e^{-TR/T_1})e^{-TE/T_2}$$

The parameters TR (recovery time) and TE (echo delay time) are under the control of the operator of the MR imaging system, and are constants for any given image. However, $T_1$ and $T_2$ are functions of the tissue under examination, and therefore vary with position in the x-y plane. By suitable selection of parameters TR and TE, either the $T_1$ or the $T_2$ term in the above equation can be made to dominate, thereby producing so-called "$T_1$-weighted" and "$T_2$-weighted" images, respectively. Other imaging methods, although very effective, have lower resolution and are not nearly as effective in presenting real time data compared to MRI. For example, gamma cameras performing Single Photon Emission Computed Tomography (SPECT) have been utilized in nuclear medicine for some time, but with introduction of high speed digital computer systems for image acquisition as well as image reproduction, images could be acquired and analyzed almost instantaneously. However, SPECT camera systems utilize a collimator that is installed in front of the scintillation crystal within a scintillation detector. The collimator is used to collimate the incoming gamma rays so only those rays of a certain angle of incidence actually penetrate the crystal. Although SPECT imaging is extensively used in nuclear medicine and provides beneficial image quality, the collimator introduces a source of image degradation in nuclear medicine images and tends to somewhat reduce the resolution and quality of images acquired by SPECT systems. For these reasons, the MRI was chosen to follow organic and geometric changes in the airways during aerosol administration.

The respiratory system principally supplies oxygen to the body and removes carbon dioxide from venous blood. It also removes atmospheric contaminants and particulate matter in inspired air entering the large, conducting airways of the respiratory tract. This becomes especially problematic for drugs that are administered by be inhalation to the lung to treat local as well as systemic diseases. Drugs and a variety of insoluble particles that deposit in the conducting zones of the airways may clear out largely by mucocilliary clearance and the cough reflex mechanism, or by endocytosis [Oberdoster G. Lung clearance of inhaled insoluble and soluble particles. J. Aerosol Med. 1988; 1: 289–330]. Therefore, inhaled particles, i.e., cellular debris, degraded myelinate surfactant materials, micro-organisms, and fine particulate drug matter most often are unable to enter the lower and peripheral airways of the lung. If these particles successfully escape the filtration mechanisms of the lung, they could enter the alveoli and acini depending on their size and deposition characteristics.

The lung contains three basic components, namely air, blood and tissue. The architectural arrangement of these three basic components provides optimal conditions for gas exchange and efficient resistance to the movement of air and blood. But a principle function of the lung is to provide for efficient removal of particulate matter in inspired air by a highly specialized transport mechanism referred to as mucocilliary clearance. This is a homeostatic process that can have significant impact on lung drug delivery. Furthermore, the effect of transient changes in airway geometry during the inspiratory maneuver could have considerable impact on drug deposition as well as transport of aerosolized particles from the conducting airways to the respiratory, peripheral lung. To the degree that this is possible, pharmacological actions of inhaled drugs could be significantly altered at their sites of action in the lung or systemically elsewhere in the body. Implications of upper airway anatomy and physiology on morphology of lung drug delivery may be found elsewhere Kilburn K. H., "Functional Morphology of The Distal Lung", Int. Rev. Cytol. 37 (1974) 153–270. But it is noteworthy that after the oropharynx, the lung splits off dichotomously through 23 generations or branches beginning with the trachea, each subsequent pair of branches having a smaller diameter than that of the parent. A widely used model for describing these geometric and morphologic changes may be obtained from Weibel and others [Weibel, E. R., "Morphometry of the Human Lung", Springer-Verlag, Berlin, (1963) pp. 1–151; Bouhuys A., "The Physiology of Breathing", Grune & Stratton, 1977, New York, pp. 60–79; 173–232]. Thus, after escaping interception and impaction on the tongue, palate, and larynx, the inhaled particle must travel through a series of tubes with increasing resistance and decreasing diameter. The geometric configuration of the tongue base, and the upfront narrowing of the air gap between the posterior pharyngeal wall and the posterior surface of the tongue base become the first line of defense for the body. Accordingly, the probability with which the inhaled particle is removed from the inspired air before it even has the chance to enter the trachea is greatest in the oropharynx. Thus, it is a significant problem for inhaled drugs to escape filtration mechanisms of the oropharynx during aerosol administration as a normal, homeostatic reflex mechanism triggers interception of solid particles by action of the tongue and palate.

In addition to particulate interception in the oropharynx, the body uses the gag and cough reflexes to functionally remove harmful solids from the inspired air. Additionally, the upper airway produces mucous that traps particles in the air during inspiration and transports them as sputum to the mouth where they are unconsciously swallowed. Reflex action during inhaled drug delivery that provokes swallowing may result in a significant portion of medicament entering the esophagus rather than the lung.

It is therefore a problem for most inhaled aerosols to retain much of their drug payloads in the inspired air until they reach the peripheral lung as a substantial amount of the aerosol cloud, usually in excess of 50%, is lost to the gastrointestinal tract as a result of swallowing. For this reason, the term "medication delivery" has been devised to refer to the fraction of an aerosolized dose estimated to reach the airways of the patient. It is true that medication delivery efficiency for any aerosol product would depend largely on the device used as a dosimeter. However, gag and cough reflexes are implicated in the inefficiencies associated with aerosol products [Brain D. B., Valberg P. A., and Sneddon S., "Mechanisms of Aerosol Deposition and Clearance", in, *Aerosols in Medicine, Principles, Diagnostics and Therapy*, Morén F, Newhouse M T, and Dolovich M B (eds), Elsevier, 1985, Ch. 5] but these could be avoided largely by good technique during the dosing regime [Newman S P, Pavia D, Garland N, Clarke S W. Effects of various inhalation modes on the deposition of radioactive pressurized aerosols. *Eur. J. Respir. Dis.,* 1982; 63: 57–65]. Generally, proper training is all that may be required in order to substantially reduce dose-variability to an acceptable level. However, with regard to drugs that have a narrow therapeutic index or are too expensive to reasonably accept significant losses from swallowing, dose variability can be reduced only when good device design and good patient technique are used contemporaneously to temporarily decouple the defense mechanisms of the oropharynx [Hilton S. An audit of inhaler technique among asthma patients of 34 general practitioners. Brit. *J. Gen. Pract.,* 1990; 45: 505–506; Pedersen S, Frost L, Arnfred T. Errors in inhalation technique and efficiency in inhaler use in asthmatic children. Allergy, 1986; 41: 118–124; Orehek J, Gayrard P, Grimaud C H, Charpin J. Patient error in use of bronchodilator metered aerosols. Br. Med. J., 1976; 1:76; Newman S P, Pavia D, Clarke S W How should a pressurized β-adrenergic bronchodilator be inhaled ? *Eur. J. Respir. Dis.,* 1981; 62: 3–21].

It is also believed that besides a good device and appropriate technique, the inspiratory maneuver itself, coupled with formulation properties, (i.e., solids content in plume, energetics of aerosolized particles, size, etc), could enhance lung deposition efficiency [Phipps P R, Gonda I. Evaporation of aqueous aerosols produced by jet nebulizers: effects on particle size and concentration of solution in the droplets. *J. Aerosol Med.,* 1994; 7: 239–258; Smalldone G C. Deposition patterns of nebulized drugs: is the pattern important. *J. Aerosol Med.,* 1994: 7(suppl): 25–32; Hurley P K, Smye S W, Cunliffe H. Assessment of antibiotic aerosol generation using commercial jet nebulizers. *J. Aerosol Med.,* 1994; 7: 217–228]. Extreme differences in formulation content and flow rate for different aerosol products (i.e., DPIs, pMDIs, nebulizers) engender significant variations in patient dosing maneuvers. Understandably, these variations result in transient, geometric changes in the oropharynx thus contributing to much of the variability noted earlier for aerosol devices. For some drugs, such noted variability in dose may be acceptable from safety standpoint; however, for drugs demonstrating dose and concentration-dependent adverse events as aerosolized medicines, the liabilities may be considerable when compared with conventional routes of drug administration. For example, inhaled salbutamol and terbutaline require $\frac{1}{20}$th of the oral dose to demonstrate equivalent efficacy [E. H. Walter, *Res. Clin. Forums,* 6, 1984, 73]. Aerosolized beclomethasone diproprionate in doses of 400 µg are reported to be equivalent to 5 to 10 mg of oral prednisolone [D. Ganderton and N. M. Kassem. Dry Powders Inhalers, In: D. Ganderton and T. Jones, eds., *Advances in Pharm. Scs.,* vol. 6, Academic Press, 1992, pp. 165–191]. Effective drug doses in the lung are indeed very low, and for this reason, any significant variations in oropharyngeal removal of the labeled dose may have considerable safety and efficacy concerns.

Attempts have been made to design delivery methods that overcome the restriction caused by breathing and swallowing, but these have been of limited effectiveness. As stated, inspired medicament that impacts in the back of the throat can enter the esophagus rather than the trachea, reducing the dosage going to the desired locations. The hypopharynx leads to both the trachea anteriorly and the esophagus posteriorly. The proximity of these two tubular structures in the back of the mouth make delivery into the trachea and thus to the bronchi and alveoli difficult. This difficulty is further demonstrated by the need to align the axes of the oropharynx, hypoharynx and trachea during endotracheal intubation. Under normal conditions the upper airway is tortuous and, therefore, a poor conduit for visualizing the vocal cords, which is necessary for placement of an artificial airway in patients who are breathing inadequately. The oropharynx is large enough that an orotracheal tube can be easily misdirected by accidental insertion into anatomical spaces surrounding the larynx, such as the esophagus [Aaron E. Bair, "Method and apparatus for establishing a surgical airway, U.S. Pat. No. 5,988,168]. Similarly, the oroesophageal axis may be geometrically aligned in such a way as to be counterproductive for aerosol drug delivery such as described earlier. Furthermore, current devices and methods are generally unable to assure the exclusive passage of the aerosol cloud or mouth adapter through or into the intended orifice (the larynx or esophagus).

To overcome dose-triggering and patient inspiratory maneuver difficulties, large medicament holding chambers have been developed as ancillary device hardware for aerosol medicaments. These devices reduce oropharyngeal loss by insuring that only drug particles with a particular size range, i.e., 10 μm or less, are introduced to the orotracheal canal. For example, an auxiliary device that comprises a chamber having an inlet adapted to receive the metered-dose aerosol device, and an outlet has been described (Richard Kraemer, in "Valved auxiliary device for use with aerosol container", U.S. Pat. No. 5,427,089). A mask adapted to communicate with the nose and/or mouth of a patient, preferably an infant or young child, communicates with the chamber outlet via a first valve which permits the infant or young child to inhale aerosol-carrying air from the chamber, and communicates with atmosphere via a second valve permitting exhalation therethrough. The distance between the chamber inlet and the chamber outlet is such that the mass percentage of aerosol particles having a diameter of from 1.0 microns to 5.0 microns is substantially a maximum at the chamber outlet, and the volume of the chamber is from 200–500 ml. Such a device member is large, cumbersome, and user-unfriendly. Although it reduces the effective amount of drug swallowed by the patient, it nonetheless reduces the total medication delivery by retaining the unrespirable fraction of the aerosolized dose.

Inhalation flowrate also has been understood for some time to be an important variable in targeting delivery of inhalation aerosols to particular sites in the pulmonary system. Studies in Bryon (ed.), Respiratory Drug Delivery, CRC Press, Inc. (1990); Newman et al., Thorax, 1981, 36:52–55; Newman et al., Thorax, 1980, 35:234; Newman et al., Eur. J. Respir. Dis., 1981, 62:3–21; and Newman et al., Am. Rev. Respir. Dis., 1981, 124:317–320 indicate that during a single breath of an aerosol compound, only about ten percent of the total aerosol material presented is deposited into the lungs and that the location of deposition in the lung depends upon (1) breath parameters such as volume of inspiration, inspiratory flow rate, breath holding prior to expiration, the lung volume at the time the bolus of medication is administered, and expiratory flow rate, (2) the size, shape and density of the aerosol particles (i.e., the medicinal compound, any carrier, and propellant), and (3) the physiological characteristics of the patient. Present devices and methods cannot eliminate these variables and as such cannot control dosage administration.

A major problem with manual metered dose inhalers is that the patient frequently actuates the device at the incorrect point during the breathing cycle to obtain the benefits of the intended drug therapy or breathes at the wrong flow rate. Thus, patients may inspire too little medication, or take additional doses and receive too much medication or deliver the drug to the throat or mouth rather than the lung. Additionally, currently marketed devices typically produce aerosols with absolute velocities that are significantly higher than a patient can produce via inhalation.

A problem with breath activated drug delivery is that the dose is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with patients whose inspiratory effort is not sufficient to rise above the threshold to trigger the release valve at all.

Laube et al, U.S. Pat. No. 5,320,094, disclose a method of delivering a protein, in particular insulin, to the lungs. The method is characteristic in that an aerosolized mist of small particles is produced in an associated medicament delivery chamber. The distance from the chamber to the patient's mouth is set to slow the speed of aerosol particles entering the mouth and the flow rate through the chamber is regulated to less than about 30 liters per minute.

Tritle, U.S. Pat. No. 5,203,323, discloses an expansion chamber used in combination with a pMDI to intercept the high-velocity discharge of medicament from a pressurized inhaler. The expansion chamber has a constant volume with no moving parts or external vents for ease of cleaning, for durability and for optimizing the mist concentration. The dimensional parameters of the chamber are optimized to produce a maximum concentration of medicament mist while neutralizing the high velocity of the inhaler discharge. The chamber is provided at one end with an inlet aperture into which the inhaler mouthpiece sealingly fits. At the chamber other end is provided an outlet aperture with a chamber mouthpiece over which a user's mouth is closed. The chamber mouthpiece aperture is sized so that substantially all of the medicament mist is uniformly withdrawn during a single short breath.

Larson et al., U.S. Pat. No. 5,040,527, discloses an apparatus for dispensing a measured amount of a spray-entrapped product, typically dispensed by a metered dose inhaler device, which includes an elongated passageway having a mouthpiece portion and a main chamber portion. The metered dose inhaler is mounted between the mouthpiece and main chamber portions such that upon operation its spray is directed away from the mouthpiece. A two-position valve is provided to allow a first, low-level flow to be developed through the unit, followed by a higher flow rate as the metered dose inhaler unit is operated. This increased flow, passing through the device in the direction opposite to that of the MDI spray, contacts the spray plume to cause a high level of mixing and a decrease in spray particle size which results in a draw of the spray medication into the lungs of the user.

Zoitan et al., U.S. Pat. No. 4,926,852 discloses an apparatus for use in inhaling pharmaceutical aerosols. The apparatus includes a mouthpiece and a rigid housing for receiving an aerosolized medicine. The rigid housing has one or more orifices, which are spaced from the mouthpiece so that flow through the housing is possible but is limited by the orifice(s) to a desired volumetric flow rate.

Rubsamen, U.S. Pat. No. 5,419,315, discloses an automatic, hand-held, self-contained, portable device for delivering aerosolized drugs into the lung using a preprogrammed microprocessor that avoids overdosing but provides visual and audible signals after successful administration of a dose to the patient. Rubsamen et al, U.S. Pat. Nos. 5,364,838 and 5,672,581 also describe methods for automatically releasing a measured amount of insulin containing formulation into the inspiratory flow path of a patient in response to information obtained from determining a patient's inspiratory flow rate and volume. U.S. Pat. No. 5,906,202 describes a complex hand held device for effecting the release of medicament coordinated with inspiratory cycle information. The release point is automatically determined either mechanically or, more preferably calculated by a microprocessor which receives data from an electronic sensor. A number of parameters are measured including total lung capacity, inspiratory flow rate and inspiratory volume in order to determine how much aerosol and aerosol free air is to be released, and when in the inspiratory cycle it should be released.

Attempts have been made to solve the patient inspiration synchronization problem. U.S. Pat. No. 4,484,577 refers to using a bi-directional reed whistle to indicate to the patient the maximum rate of inhalation for desired delivery of the drug and flow restrictor to prevent the patient from inhaling too rapidly. U.S. Pat. No. 3,991,304 refers to using biofeedback techniques to train the patient to adopt a desired breathing pattern. U.S. Pat. No. 4,677,975 refers to using audible signals and preselected time delays gated on the detection of inspiratory flow to indicate to the patient when to inhale and exhale, and delivering inhalable material a selected time after the detected onset of flow.

Many other devices have been disclosed in the patent literature, nearly all of these being intended to help with dose coordination and optimization of the lung delivered dose. Most of these devices are complicated, expensive, and often require interaction between the patient and a third party during dose administration. Furthermore, they are unable to neutralize the transient defenses of the oropharynx to intercept and remove medicament from entering the trachea, thus enabling the breakthrough technology described in this application.

Drug formulation approaches have also been used as a means to improve lung drug delivery. Particle deposition in the lung is sensitive to several model-dependent factors. It is important to identify these factors when drawing general conclusions especially in regard to peripheral deposition of drug in the airways. Acute and chronic pulmonary disease can have a dramatic effect on the deposition of medicaments. Many conditions increase airway resistance, making it more difficult to deposit medication in the distal airways. Other conditions reduce lung compliance. Most changes are heterogeneous, occurring in only portions of the lung. Thus medication may go to areas of the lung that are damaged, reducing the effectiveness of pulmonary delivery. Usually, the more chronic and exacerbated the disease state, the greater also is the extent of structural and dimensional changes in the lung. These differences are known to affect airflow and particle deposition during drug therapy with inhalation aerosols [Tzila Zwas S, Katz I, Belfer B, Baum G L, Aharonson E. Scintigraphic monitoring of mucocilliary tracheobronchial clearance of technitium-99m macroaggregated albumin aerosol. *J. Nucl. Med.,* 1987, 28: 161–167]. Lung function parameters (e.g., the movement of air, both volume and velocity) are crucial factors that can affect particle deposition characteristics in patients. These lung function parameters are sensitive to a variety of disease states. For example, airway resistance is compromised in asthma and adult respiratory distress syndrome (ARDS). These disease states could alter deposition patterns of aerosolized particles to the lung compared to lung normal humans. Lung deposition studies during clinical development of aerosolized drugs should thus be carefully designed so that the effects of model-dependent variables, i.e., lung physiology and respiration rate, are kept at a minimum.

Device performance variables, when taken in concert with differences in breathing maneuvers of the patient, can contribute significant intersubject as well as intra-subject variability of the dose to lung. This problem confronts clinicians today, who, in general, tend to indict the aerosol generator or the hardware used to aerosolize these drugs. Hurley et al. showed that respirable fraction (RF) results using gentamicin as model drug with 14 commercial devices varied greatly and related the effect to the type of device used [Hurley P K, Smye S W, Cunliffe H. Assessment of antibiotic aerosol generation using commercial jet nebulizers. *J. Aerosol Med.,* 1994; 7: 217–228; Dahlback M. Behavior of nebulizing solutions and suspensions. *J. Aerosol. Med.,* 1994: 7 (suppl): 13–18]. The RF ranged between 50% with the PulmoNeb device to about 97% for a device sourced from Micro-Cirrus. Considerable differences in the mass output for formulations when nebulized at the same and constant flow rate have also been observed. Here again, the device type appears to be implicated. For example, output of sodium chloride at ~6L/min was found to be only about 60 mg/min with the Ultra Vent device. This mass output appeared to approach 300 mg/min with the Turbo Turret device although both were operated under the same flow rate conditions.

Smaldone et al. [Smaldone G C, Perry R J, Deutsch D G. Characteristics of nebulizers used in the treatment of AIDS-related *Pneumocystis carinii* pneumonia. *J. Aerosol Med.,* 1988; 1: 113–126] compared the in vitro performance of three nebulizers for the delivery of pentamidine. Each device was tested under conditions recommended for its use, e.g., specific drug concentration and breathing pattern. Apart from the size of the droplets, the potential deposition efficiency for each device was monitored. At a tidal volume of 750 cc and respiration rate of 20 breaths/min, the three nebulizers (AeroTech II, Respigard and Fisoneb) generated droplets with MMAD ranging between 0.8 and 2.5 $\mu$m. The differences appear to be significant and suggest that for each device, the deposition efficiency, i.e., the fraction of dose from the nebulizer estimated to deposit in the lung, was generally independent of drug-concentration and rather related to device performance. For example, the deposition efficiency of AeroTech II was found to be highest (~20%), followed by Fisoneb (~15%) and then Respigard (5%). The wide differences in deposition efficiency of these devices stress a need for optimal, relevant, and dose to lung discriminating specifications for nebulizers. The results also suggest that nebulized solutions must be approved with specific devices that are indicated on the label to ensure reproducible dose delivery to the peripheral lung.

Thus, precision delivery, control, and repeatability of the dosing maneuver, and systematic estimation of dose to lung, i.e., medication delivery, is a problem for most inhaled medicines. Clearly, inhalation devices should be designed to accommodate these issues. Of particular importance is the development of a device that would ensure targeted delivery of inhalation aerosols over a broad range of patient use patterns and anatomical makeup. Therefore, a method which can be used to acquire information regarding patient performance including the dynamic aspects of anatomical features and flowrate information could be instrumental in evolving device design and improving the precision of targeted pulmonary medication delivery. This disclosure utilizes imaging techniques to identify changes in physiological and geometric alignment of the oropharynx as a means to systemize drug doses received by patients.

It is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

SUMMARY OF THE INVENTION

It is therefore an object of the present invention to provide a method for using a dynamic real-time imaging technique to identify and measure geometric, spatial and anatomical changes in the oropharynx, trachea and/or upper regions of the lungs during aerosol medicament administration.

It is therefore a further object of the present invention to provide a method for measuring inhalation flow rate contemporaneous with a temporal real-time imaging technique that identifies and measures geometric, spatial, and anatomical changes in the oropharynx, trachea and/or upper regions of the lungs during aerosol medicament administration to the body.

It is therefore a still further object of the present invention to use the inhalation flow rate and measured geometric, spatial, and anatomical changes in the oropharynx, trachea and/or upper regions of the lungs during aerosol medicament administration to establish a data base which can yield design criteria for efficient drug delivery.

It is therefore a still further object of the present invention to use the inhalation flow rate and measured geometric, spatial, and anatomical changes in the oropharynx during aerosol administration to establish a data base which can yield an aerosol administration procedure that is insensitive to the gag and cough reflexes so that aerosolized medicament exiting an aerosol generator effectively escapes the filtration and swallowing mechanisms of the oropharynx.

To attain the objects described, there is provided a method comprising the use of magnetic resonance imaging (MRI) where a magnet creates a static magnetic field sufficient to extend along the long (mouth-to-larynx) axis of the patient's head. The method can also be used to produce images in the upper regions of the lungs and the lower trachea.

Because different types of tissues have different proton densities, different tissue types in the oropharynx, trachea, and lungs will have different image intensities, and therefore appear as distinct structures in the MR image. When this is coupled with the rapid rate at which images are captured, it is evident that the present inventive method provides for the capture of the real-time mobility of these structures during aerosol administration.

The present method also provides flow rate data on medicament administered based upon pressure changes within a testing mouthpiece. The pressure change data is gathered contemporaneous with the capturing of real-time MR images.

The present inventive method enhances understanding of impaction, filtration, and oropharyngeal deposition of inhaled drugs thus allowing quantitation of drug dosimetry based upon geometric and spatial configuration of the larynx/hypopharynx in the anterior-posterior (AP) as well as the cranio-caudal direction during aerosol administration. This method could be further enhanced to evaluate differences between genders, age groups, and healthy volunteers versus patients. This new understanding of the delivery is used to establish a data base of aerosol administration establishing a criteria that can be used to optimize drug delivery to the lungs through better design of delivery devices.

BRIEF DESCRIPTION OF THE DRAWINGS

Thus by the present invention its objects and advantages will be realized the description of which should be taken and in conjunction with the drawings wherein:

FIG. 2 depicts the testing setup for flow measurement when using the inventive method;

FIG. 6 is a dynamic MR image showing a patient "puffing in";

FIGS. 7 and 8 are dynamic MR images of a patient using an aerosol deliverant showing further inspiration;

FIGS. 9–17 show dynamic MR images of a patient during breathhold;

FIGS. 18–23 show dynamic MR images of a patient during slow expiration; and

FIGS. 24–26 show dynamic MR images of a patient at the end of expiration.

DETAILED DESCRIPTION OF THE PREFERRED EMBODIMENT

Figure 1A:
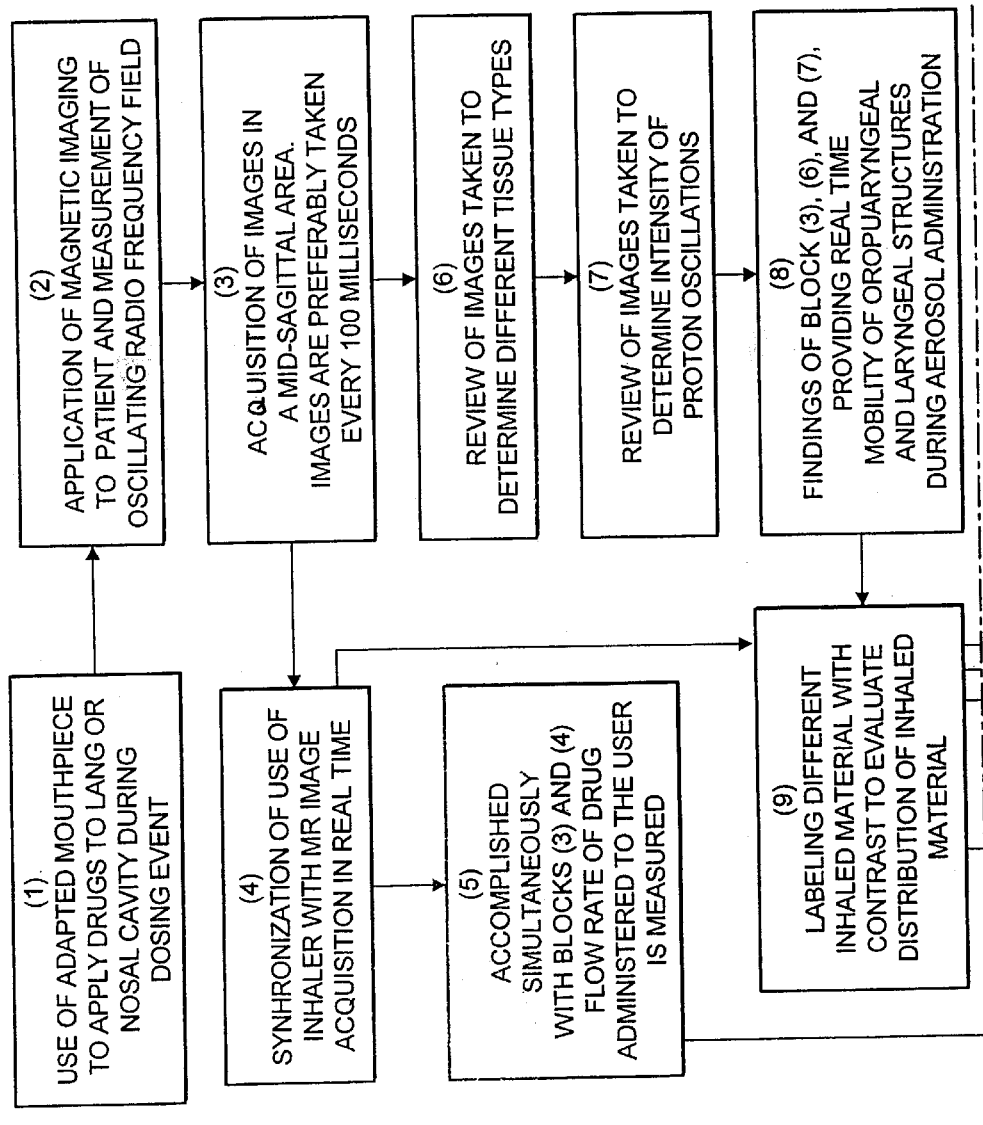
FIGS. 1a–1b are flow charts depicting the steps of the inventive method, from the application of aerosolized particles to the design criteria for more efficient drug delivery.
Figure 1B:
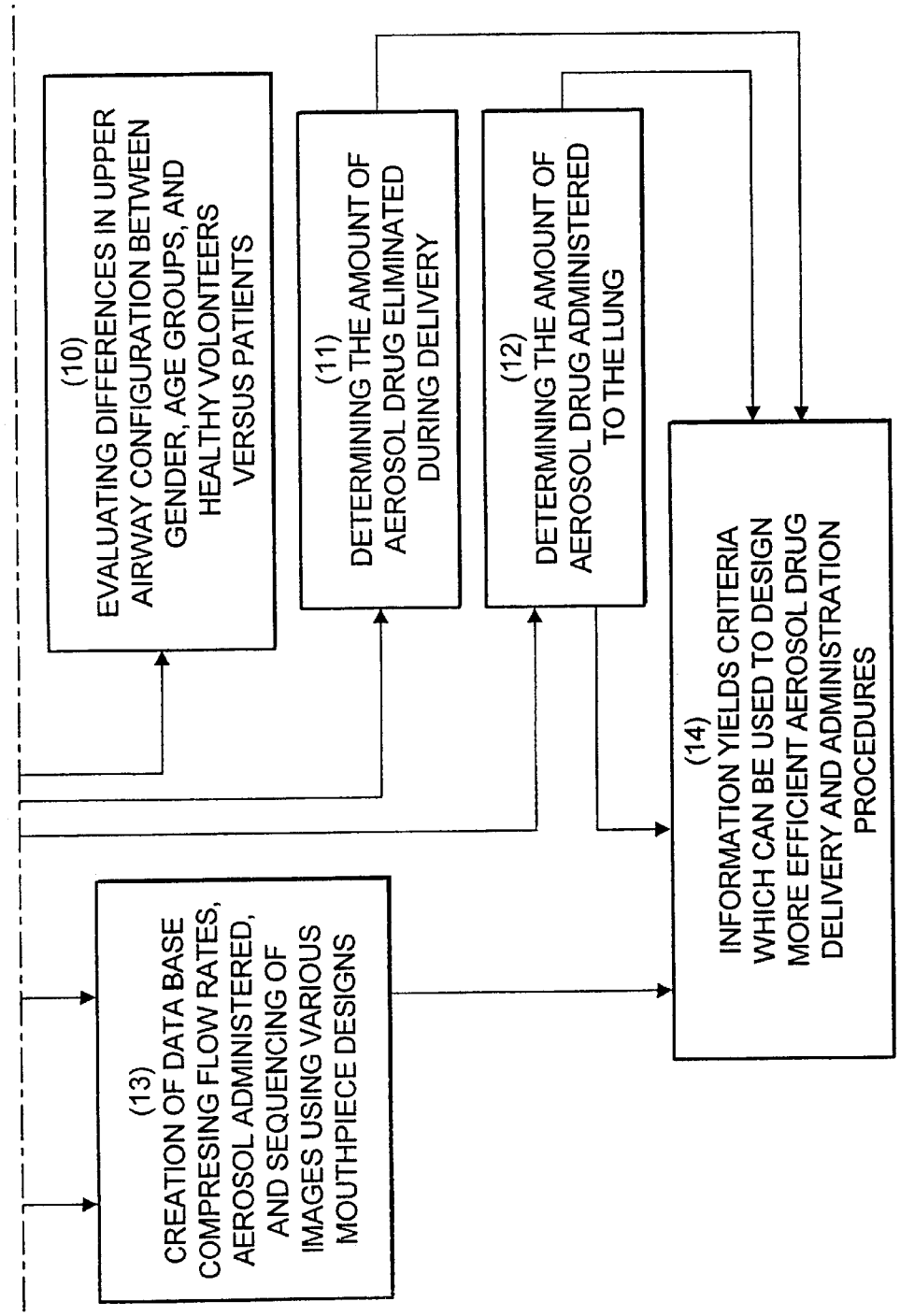
Figure 5:
FIGS. 3, 4, and 5 are dynamic MR Images (taken at 5 images/second) for a particular patient using an aerosol deliverant during inspiration.
Figure 4:
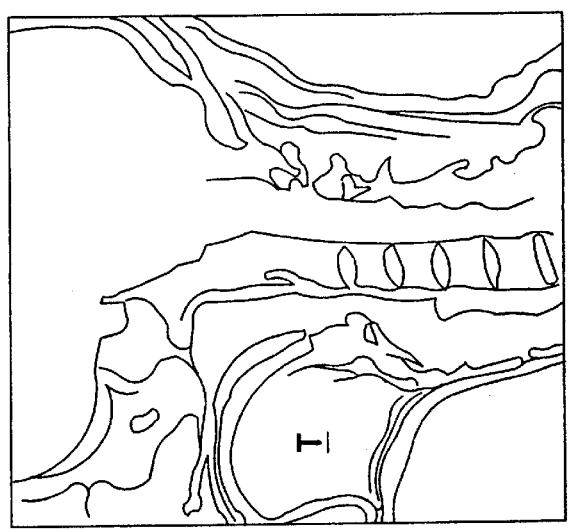
Figure 3:
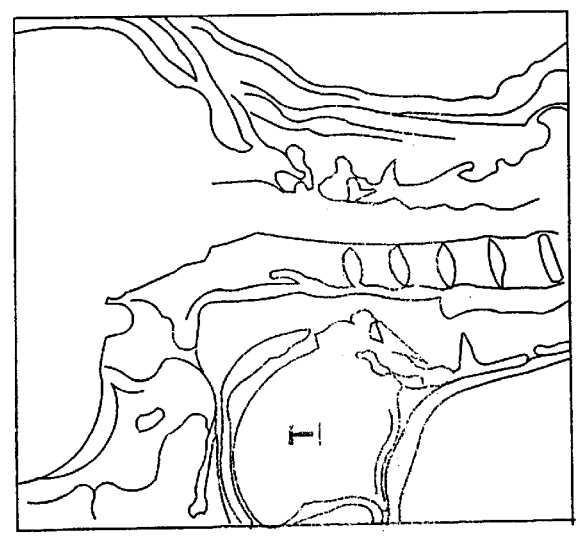
Figure 14:
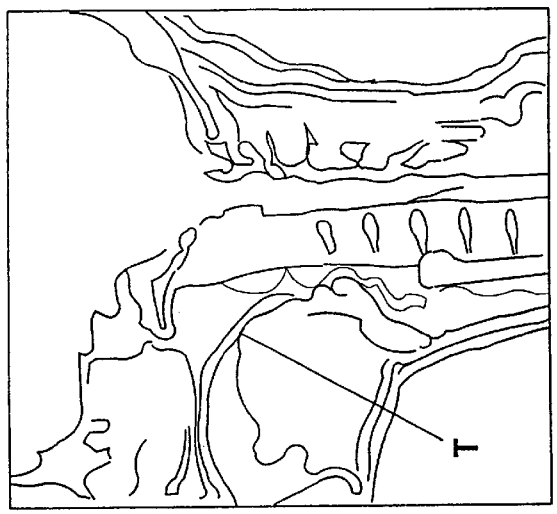
Figure 13:
Figure 12:
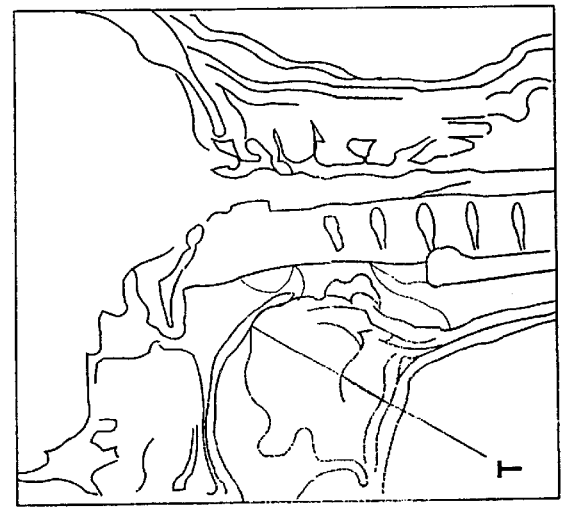
Figures 21, 22, 23:
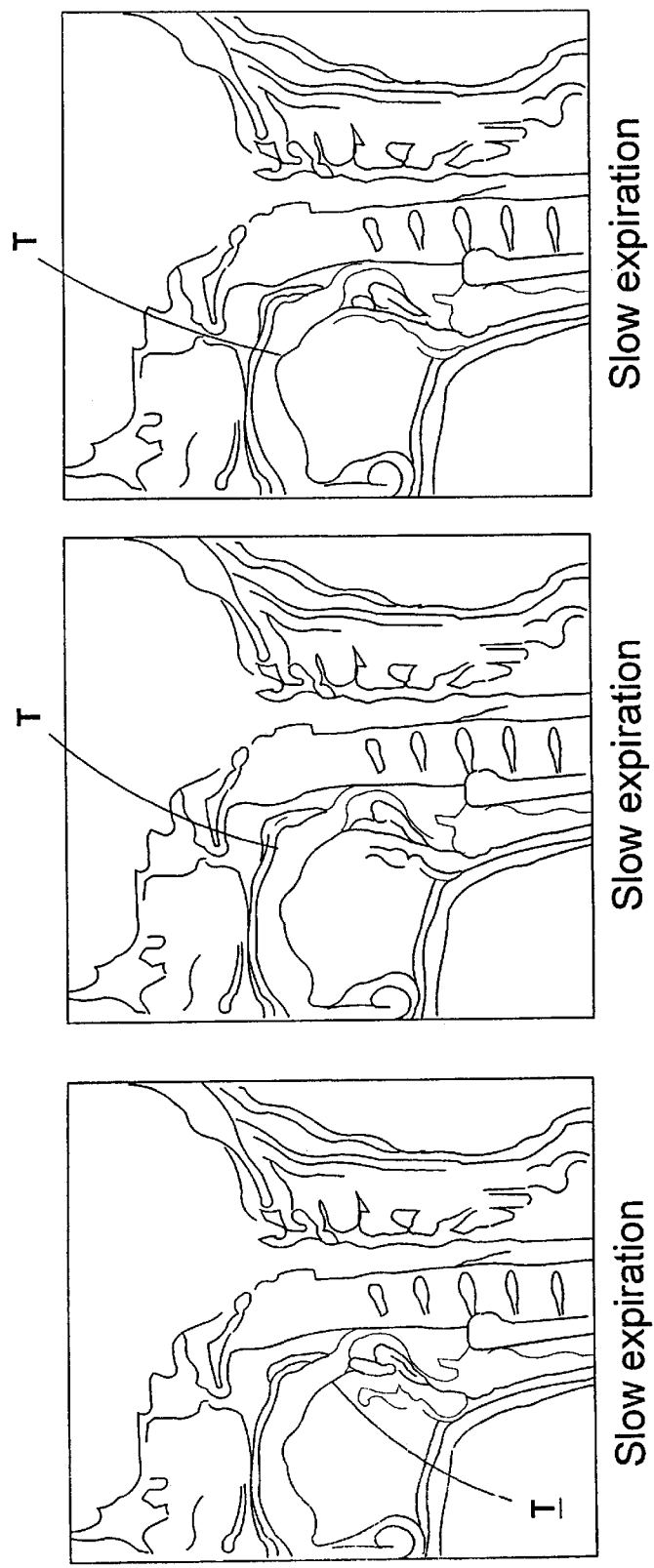

Referring now to the drawings in detail, FIG. 1 is a flow chart of the inventive method.

Block 1 indicates the use of an inhaler 12 whose mouthpiece 14 has been adapted for the purpose of measuring flow through inhaler 12 (shown in FIG. 2). The mouthpiece 14 is used to interface the aerosol drug delivery device to the oral or nasal cavity during a dosing event. A canister 10 containing an aerosol formulation including a contrasting agent such as gadolinium, or other substance suitable for purpose, producing a plume through mouthpiece 14 would be the preferred method of administration. However, alternative methods, suitable for purpose may be used.

Block 2 of FIG. 1 is the application of magnetic imaging to the patient. This application is simultaneous with the application in Block 1. The patient is placed within the bore of a large circular magnet. An antenna is positioned within the bore of the magnet and is used to create an oscillating radio-frequency field that selectively excites hydrogen atoms in the patients head to detect images of the oropharynx and trachea relative to the lips of the patient.

The oscillations are measured throughout a three-dimensional area such that when the intensities are displayed as a function of position, the result is an image very similar to the actual anatomic features in that area.

Block 3 indicates the preferred MR image acquisition. Images may be acquired using time and weighting sequences that allow acquisition of images at least 50 to 1200 milliseconds apart, but preferably an image is taken every 100 milliseconds. The method should also acquire midsagittal images in a three-dimensional area to observe changes in the configuration of the nasopharynx, oropharynx, larynx, and hypopharynx over time. At the onset of the study, axial "scout" images should be taken through the upper airway to document normal variants of airway anatomy as well as to detect any abnormalities. Dynamic images should be taken of the mid-sagittal area in resting and then with the use of the inhaler 8.

Block 4 of FIG. 1 represents the synchronization of the actuation of inhaler 8 and subsequent plume development with MR image acquisition. MR images of a three-dimensional area are synchronized with the production and flow of labeled aerosol (e.g., using gadolinium ) from inhaler 8 in real-time. Dynamic imaging with the use of inhaler 8 is repeated to determine variations in the use of inhaler 8 between different test subjects. Dynamic imaging operation would be performed using inhalers with different attributes (e.g., pressure drop, mouthpiece shape, etc.) to determine their effectiveness as a delivery mechanism as will be discussed.

Block 5 is accomplished simultaneously with the MR image acquisition of Block 3 and the inhaler use of Block 4, wherein Block 5 measures the flow rate during inhalation. Flow rate is determined through the use of an inhaler 8 as shown in FIG. 2. The patient would depress canister 10 in the inhaler 12 while inhaling through mouthpiece 14. When the patient inhales through inhaler 8 provided that there is at least some minimal restriction, the pressure at mouthpiece 14 will be lower than the pressure surrounding the inhaler 8. In this case, inhaler 8 is acting as a Venturi producing a differential pressure which can be converted by equation to determine flow rate.

When monitoring the pressure changes in adapted mouthpiece 14, dual lumen tubing 18 is routed from the device 8 to outside the MRI chamber to an electronic differential pressure transducer 20. Single lumen tubing may also be used provided the pressures are equal between the MRI chamber and the location of pressure transducer 20. One bore at end 19 of tubing 18 connects to pressure port 22 and another bore at end 19 of tubing 18 is open to atmosphere. Both bores at the other end 24 of tubing 18 are connected to pressure transducer 20. The pressure measurement range of pressure transducer 20 is matched to the maximum pressure drop in mouthpiece 14 based on maximum flow through inhaler 8 and known resistances in mouthpiece 14. Pressure transducer 20 is interfaced to a personal computer 26. Personal computer 26 acquires the pressure signal via tubing 18 and pressure transducer 20 and an analog to digital convertor. Personal computer 26 then with the appropriate algorithm converts the pressure data to flow data. Calculations of flow rate are contemporaneous with acquisition of the MR image sets. This integration is effected using an appropriate electronic trigger from the MR equipment to the personal computer 26. Similar devices that are suitable for this purpose may be used for determining the flow rate during inhalation and drug administration.

Block 6 is a review of the images taken, to determine different tissue types. Since different types of tissues have different proton densities, different tissue types have different image intensities based on their physical and chemical properties and therefore appear as distinct structures in the MR image.

Block 7 is a review of the images taken specifically the intensity of proton oscillations. The intensity of proton oscillations at a given point in the patient's body is proportional to the proton density at that point so that geometric alignment, spatial configuration, volumetric descriptors could be applied to the tissues and organs in the orpharynx; therefore, an assessment of the impact of geometric and spatial orientation of the orpharynx or trachea can be determined during inhalation through an aerosol drug delivery system.

Block 8 couples the findings of Blocks 3, 4, and 5 to provide a capture of the real-time mobility of oropharyngeal and laryngeal structures during inhalation through an aerosol drug delivery system.

Block 9 indicates a capability to label different inhaled material with some type of contrast to evaluate the distribution of the inhaled material as it should be visible as a plume being inhaled or a coating on the mucosa. This would be best obtained with images in a three-dimensional area from the nasopharynx to trachea, or potentially even lower if possible.

Block 10 indicates that with the capability of real-time MR imaging during the use of inhaler 8 of FIG. 2, differences in the inhalation techniques can be determined between genders, age groups, and healthy volunteers versus patients.

Block 11 of FIG. 1 indicates that after a review of the imaging, the amount of aerosol drug eliminated during delivery can be determined.

Block 12 indicates that after a review of the imaging, the amount of aerosol drug administered to specific areas in the lung can be determined.

Block 13 is the creation of a database of flow rates during the acquisition of various MR images with amounts of aerosol drugs in the images indicated. The database is created by integrating the MRI computer with personal computer 26 of FIG. 2. The database will also indicate this information for various device attributes along with different types of medicine being dispensed. For example, for a particular dispenser and mouthpiece combination, X percent of the medicine being dispensed is delivered to targeted locations in the lungs. This provides an objective standard that can be referred to when designing the delivery device for a particular medicine. In addition, dose requirements can be determined and repeatability achieved.

Block 14 is the final stage where the information from capturing the real-time mobility of oropharyngeal and laryngeal structures during inhalation through an aerosol drug delivery system, the state of aerosol drug delivered, and the database which is obtained from the practice of this method can yield the criteria that can be used to design more efficient aerosol drug delivery to optimize the amount of the particular medicine to be delivered to the specific targets in the lung. This criteria can also be used to develop an aerosol administration procedure that is insensitive to gag and cough reflexes of the body so that aerosolized medicament exiting an aerosol generator effectively escapes filtration and swallowing mechanisms of the oropharynx.

FIGS. 3–26 are dynamic images taken of a single patient. Note that while two-dimensional images are shown, as will be readily apparent to the skilled artisan, the information regarding these images can be manipulated or otherwise used to create 3-D images providing volume and other viewing perspectives. In general, these images depict the capture of changes in size and shape of the upper airway during the use of an inhaler over the course of inspiration, breathhold, and expiration. As indicated in FIG. 1, the collection and analysis of this information from a representative sampling of patients will be useful in establishing a database.

FIGS. 3–8 which depict the shape of the upper airway during inspiration, it can be seen that the tongue T creates a blockage or occlusion near the roof of the mouth and in the larynx.

FIGS. 9–17 which depict the shape of the upper airway during a breathhold, it can be seen that the tongue T creates a complete blockage near the back of the roof of the mouth.

FIGS. 18–23 which depict the shape of the upper airway during a slow expiration, it can be seen that tongue T no longer blocks the roof of the mouth or the larynx.

FIGS. 24–26 which depict the shape of the upper airway at the end of expiration, it can be seen that the tongue creates a noticeable blockage near the roof of the mouth or larynx.

In addition, it is envisioned that coupled with the foregoing method and information obtained thereby, is the use of existing nuclear medicine methodologies for tracing the medicine being dispensed as it passes through one's air ways and is deposited at various sites along the administration route. Accordingly, included in the dispensed material would be a trace element (e.g., gadolinium, technetium) the presence of which can be monitored in the body through the use of appropriate imaging tools. After collecting the MRI and flow data pertaining to the inhalation and administration of the dispensed material containing the trace element, the patient would then be imaged using an appropriate nuclear medicine tool (e.g., gamma camera). Information pertaining to the locations where the material is deposited and to the relative amounts of this material in each location would be generated. Such information, when combined with the dynamic MR image and inhalation flow data, will enhance the understanding of the effectiveness of a particular aerosol delivery system in administering medicine to targeted pulmonary sites as well as the dose size necessary for effective treatment, among other things.

Thus by the present invention its objects and advantages are realized and although preferred embodiments have been disclosed and described in detail herein, its scope should not be limited thereby, rather its scope should be determined by that of the appended claims.

What is claimed is:

1. A method for identifying and measuring geometric, spatial, and anatomical changes in real-time in airway structures in a mammal during inhalation comprising the steps of:

- using a magnetic resonance imaging device (MRI) to produce real-time dynamic images from said magnetic resonance imaging at a rapid rate thereby depicting the mobility of the airway structures during inhalation;
- applying geometric alignment, spatial configuration, and volumetric descriptors to the different type of images produced with said magnetic resonance imaging;
- evaluating such imaging to determine the anatomical changes in the airway structures during inhalation; and
- wherein inhalation takes place through a mouthpiece used to dispense a substance which comprises an aerosol medicament, placebo or air.

2. The method of claim 1 wherein said substance includes a contrasting agent.

3. The method of claim 2 wherein the contrasting agent is gadolinium.

4. The method of claim 2 wherein the contrasting agent is technetium.

5. The method of claim 1 which further includes the step of magnetic resonance imaging the upper regions of the oropharyngeal, lower trachea and lungs of the mammal to determine flow of the substance within the airway structures.

6. The method of claim 1, further including the step of determining the flow rate during inhalation and correlating the flow rate data with the real-time imaging.

7. The method of claim 5, further including the step of determining flow rate data of inhalation and correlating the flow rate data with the real-time imaging.

8. The method of claim 6, wherein the flow rate data is determined simultaneously with the production of said real-time images.

9. The method of claim 7, wherein the flow rate data is determined simultaneously with the production of said real-time images.

10. The method of claim 6, further including the step of using said imaging and said flow rate data in determining design criteria for aerosol delivery devices.

11. The method of claim 7, further including the step of using said imaging and said flow rate data in determining design criteria for aerosol delivery devices.

12. The method of claim 6, further including the step of using said imaging and said flow rate data to establish a database of information for a plurality of delivery devices.

13. The method of claim 7, further including the step of using said imaging and said flow rate data to establish a database of information for a plurality of delivery devices.

14. The method of claim 4, further including the step of determining an amount and location of the substance being dispensed into the airway.

* * * * *